United States Patent [19]

Elliott

[11] Patent Number: 4,605,775

[45] Date of Patent: Aug. 12, 1986

[54] SYNTHESIS OF HIGHER KETONES

[75] Inventor: David J. Elliott, Bartlesville, Okla.

[73] Assignee: Phillips Petroleum Company, Bartlesville, Okla.

[21] Appl. No.: 725,843

[22] Filed: Apr. 22, 1985

[51] Int. Cl.$^4$ ............................................. C07C 45/72
[52] U.S. Cl. .................................................. 568/387
[58] Field of Search ............... 568/403, 387, 388, 361; 423/656

[56] References Cited

U.S. PATENT DOCUMENTS

| | | | |
|---|---|---|---|
| 2,046,145 | 6/1936 | Arnold | 568/403 |
| 2,419,142 | 4/1946 | Ipatief et al. | 568/388 |
| 2,526,742 | 10/1950 | Gresham et al. | 568/387 |
| 2,670,378 | 2/1954 | Frye | 568/387 |
| 3,014,962 | 12/1961 | Reppe et al. | 260/532 |
| 3,153,068 | 10/1964 | Porter et al. | 568/403 |
| 3,361,828 | 1/1968 | Robbins et al. | 568/403 |
| 3,615,217 | 10/1971 | O'Brian et al. | 423/656 |
| 3,790,505 | 2/1974 | Casey et al. | 252/463 |
| 3,829,495 | 8/1974 | Mizutani et al. | 260/586 R |
| 3,946,079 | 3/1976 | Mizutani et al. | 260/593 R |
| 4,126,581 | 11/1978 | Sugier et al. | 423/656 |
| 4,212,825 | 7/1980 | Nissen et al. | 568/313 |
| 4,289,911 | 9/1981 | Isogai et al. | 568/387 |
| 4,339,606 | 7/1982 | Kuang et al. | 568/396 |

Primary Examiner—James H. Reamer
Attorney, Agent, or Firm—K. K. Brandes

[57] ABSTRACT

Higher ketones prepared by contacting under suitable reaction conditions a feed stream comprising (a) a lower ketone having 3–5 carbon atoms per molecule and (b) carbon monoxide with a catalyst composition comprising copper oxide, zinc oxide and, optionally, alumina. The formed higher ketones contain at least one carbon atom per molecule more than the lower feed ketone, preferably methyl ethyl ketone.

21 Claims, No Drawings

SYNTHESIS OF HIGHER KETONES

BACKGROUND OF THE INVENTION

This invention relates to a catalytic process for preparing ketones. In another aspect, this invention relates to the conversion of lower ketones to higher ketones.

Catalytic processes for converting lower ketones to higher ketones, e.g. by dimerization, are known. Such processes are disclosed in U.S. Pat. Nos. 4,339,606; 4,212,825 and 3,946,079. However, there is an ever present need to develop new processes employing different catalysts and reaction conditions and resulting in different product distributions or different yields of specific ketones.

SUMMARY OF THE INVENTION

It is an object of this invention to catalytically convert lower ketones to higher ketones. It is another object of this invention to convert lower ketones having 3-5 carbon atoms per molecule to ketones having at least one carbon atom per molecule more than said lower ketones. It is a further object of this invention to convert methyl ethyl ketone to at least one ketone having at least 8 carbon atoms per molecule. Other objects and advantages will be apparent from the detailed description and the apended claims.

In accordance with this invention, a feed mixture comprising (a) at least one ketone having from 3 to about 5 carbon atoms per molecule and (b) carbon monoxide is contacted with a catalyst composition comprising copper (II) oxide and zinc oxide, under such conditions as to at least partially convert said ketone to at least one higher ketone having at least one carbon atom per molecule more than the feed ketone in said mixture, and preferably having at least 6 carbon atoms per molecule. In one embodiment, the catalyst composition in the process of this invention comprises a copper (II) oxide, zinc oxide and an inorganic refractory oxide support material (e.g., alumina). In one preferred embodiment, the catalyst composition comprising CuO and ZnO is pretreated by heating with a reducing gas, preferably a free hydrogen containing gas, under such conditions as to partially reduce CuO to $Cu_2O$ and/or Cu metal, before the catalyst composition is used in the process of this invention. In another embodiment, a gaseous mixture of methyl ethyl ketone and CO is passed over a $CuO-ZnO-Al_2O_3$ catalyst composition (preferably having been pretreated by heating with a free hydrogen containing gas), under such reaction conditions as to produce mainly 5-methyl-heptanone-3.

DETAILED DESCRIPTION OF THE INVENTION

The catalyst composition employed in the process of this invention comprises an oxide of copper and an oxide of zinc. Preferably the mixed oxide is prepared by coprecipitation of either the hydroxides of copper and zinc and/or the carbonates of copper and zinc, e.g. by addition of a base such as NaOH, or a soluble carbonate such as $Na_2CO_3$, to an aqueous solution of copper and zinc salts such as nitrates, halides or sulfates of copper and zinc, and subsequent calcination (heating in air) under such conditions as to form the oxides of copper and zinc. In a preferred embodiment, an inert support material such as alumina is also present in said catalyst composition, preferably prepared by either coprecipitation of hydroxides and/or carbonates of copper, zinc and aluminum and subsequent calcination under such conditions as to form the oxides of copper, zinc and aluminum; or by coprecipitation of hydroxides and/or carbonates of copper and zinc from an aqueous solution containing dispersed alumina, and subsequent calcination; or by the method described in U.S. Pat. No. 3,790,505, herein incorporated by reference. $CuO-ZnO$ containing catalyst compositions are commercially available from United Catalysts, Inc., Louisville, Ky. and from BASF Wyandotte Corporation, Parsippany, N.J.

In a preferred embodiment, the $CuO-ZnO$ and $CuO-ZnO-Al_2O_3$ catalyst compositions are pretreated by heating with a reducing gas, preferably a free hydrogen containing gas, so as to partially reduce CuO. More preferably, said heating is carried out with a free hydrogen containing gas, most preferably a $H_2/N_2$ mixture containing 2-5 volume % $H_2$, at about 350°-450° F. for about 1-6 hours.

Preferably the weight ratio of CuO to ZnO ranges from about 1:20 to about 20:1, more preferably from about 1:3 to about 3:1. If alumina ($Al_2O_3$) or another inert refractory material (e.g., silica, an alumino-silicate, titania, magnesia and the like) is also present in said catalyst composition, the weight ratio of said inert material such as alumina to (CuO plus ZnO) can range from about 1:100 to about 10:1, preferably from about 1:10 to 2:1. Generally the surface area (determined by the $BET/N_2$ method, ASTM D3037) of the catalyst composition ranges from about 20 $m^2/g$ to about 300 $m^2/g$, preferably from about 50 $m^2/g$ to about 200 $m^2/g$.

The gaseous feed mixture that is contacted with the $CuO-ZnO$ containing catalyst composition comprises (a) at least one ketone having from 3 to 5 carbon atoms per molecule and (b) carbon monoxide. The volume ratio of the ketone vapor (having 3-5 carbon atoms per molecule) to carbon monoxide in the feed generally ranges from about 1:100 to about 20:1, preferably from about 1:20 to about 1:1, measured at about 550° F. and 15 psia. An inert gas such as nitrogen or helium can also be present in said feed stream. The preferred ketone is methyl ethyl ketone.

The ketone and CO containing mixture can be contacted with the $CuO-ZnO$ containing catalyst composition in any suitable manner. A stream containing a vaporized ketone having from 3 to 5 carbons and a carbon monoxide containing stream can be passed separately into a suitable reaction vessel and can then be contacted in at least partially mixed form with the catalyst composition under suitable reaction conditions. The ketone containing feed stream can be fed as a substantially liquid stream, which will then vaporize in the reactor, or as a substantially vaporized stream. Or the two streams can be premixed and then be contacted with the catalyst composition under suitable reaction conditions so as to produce a reaction product comprising at least one ketone containing at least 1 carbon atom per molecule more than the feed ketone. The process of this invention can be carried out as a batch process or as a continuous process. In a batch process, the process ingredients are charged in any order to a vessel equipped with pressuring and heating means, and the ingredients are then kept in contact with the catalyst composition for a certain length of time under suitable reaction conditions so as to produce a product comprising at least one ketone containing at least 1 C atom per molecule more than the feed ketone. In this type of operation, the catalyst can be dispersed in the gaseous feed stream as a fluidized bed; or the gaseous feed stream can be circulated through a fixed bed containing the catalyst composition. In a continuous process, which is presently preferred, the ketone and CO containing gaseous feed stream can be passed, at least partially mixed, through a fixed bed containing the solid catalyst composition, under such conditions as will result in a product comprising at least one ketone containing at least 1 C atom per molecule more than the feed ketone. Optionally, an inert gas can be present during the batch or continuous process.

Heating of the process ingredients is generally required to accomplish at least partial conversion of a ketone containing from 3 to 5 C atoms to a ketone containing at least one additional carbon atom per molecule. Any suitable temperature that will cause and maintain a controllable reaction can be employed. Any feasible heating means can be utilized. It is within the scope of this invention to preheat one or more of the process ingredients before they are introduced into a reactor, which is heated to maintain a suitable temperature. The reaction temperature generally ranges from about 200° C. to about 400° C., preferably from about 250° C. to about 300° C.

The reaction pressure generally is above atmospheric pressure. The selection of the reaction pressure will greatly depend on the reaction temperature, the feed rates of feed and the specific reactor design. Generally the pressure ranges from about 1 psig to about 5,000 psig, preferably about 200 psig to about 2,000 psig.

The reaction time, i.e., the time of intimate, simultaneous contact of all process ingredients, can vary from 0.01 to about 60 minutes and will preferably be in the range of about 0.1 to about 10 minutes. The actual reaction time will greatly depend on the flow rates of the ketone and CO containing feed stream, the selection of an effective, yet safe reaction temperature, the extent of mixing and agitation (if any) during the reaction and the amount of the catalyst employed. In a continuous process, the gas hourly space velocity of the combined feed stream comprising the ketone and CO ranges generally from about 100 to about 10,000 cc feed stream/cc catalyst/hour, preferably from about 1,000 to about 5,000 cc/cc/hr, measured at about 550° F. and 25 psia.

The formed reaction product which comprises at least one ketone containing at least one C atom per molecule more than the feed ketone can be separated from the reaction mixture by any suitable separation means such as condensation, crystallization, absorption, fractional distillation, or extraction with a suitable solvent plus subsequent evaporation of the solvent. Unreacted process ingredients can be at least partially separated in a similar manner and can be recycled to the reaction zone where the conversion of lower ketones to higher ketones in accordance with this invention occurs.

If a reaction product containing more than one ketone is formed, said product can be separated into the pure components by any of the above-cited or other known separation means. Compositions of products formed from the preferred ketone, methyl ethyl ketone, under specific reaction conditions are presented in the Examples. Ketones prepared by the process of this invention can be used as solvents and/or as reactants in various organic synthesis.

The following examples are presented to further illustrate this invention without unduly limiting the scope of the invention.

EXAMPLE I

This example illustrates the conversion of methyl ethyl ketone and carbon monoxide to higher ketones in the presence of a 16/14 mesh $CuO-ZnO-Al_2O_3$ catalyst prepared substantially in accordance with the procedure of Example I of U.S. Pat. No. 3,790,505, herein incorporated by reference. The reactor used was a vertical, tubular, stainless steel reactor having an inner diameter of about one-half inch and a catalyst bed length of about 5–6 inches, and was heated by means of an outside furnace. The reactor was filled as follows: top layer of 5 cc 16 mesh Alundum (having a surface area of less than 1 m²/g; marketed by Norton Chemical Process Products, Akron, Ohio); middle layer of 2.5 cc (3.0 g) of the $CuO-ZnO-Al_2O_3$ plus 7.5 cc 16 mesh Alundum; bottom layer of 5 cc 16 mesh Alundum. A thermocouple was axially inserted into the catalyst bed.

First the catalyst bed in the reactor was pretreated with a $H_2/N_2$ (3/97) gas mixture at about 390°–400° F., for a time period of about 4 hours. Then the reactor was purged with nitrogen, the temperature was raised to 550°–555° F., and two feed streams were charged to the reactor: liquid methyl ethyl ketone at a rate of 1.5–2.3 cc/hr, and either carbon monoxide (99.5%) or nitrogen at a rate of 140 cc/min, so as to provide a combined gas stream containing about 90 volume % CO or $N_2$. The product stream was cooled by a cold trap having a temperature of about 30° F., so as to condense the less volatile components. The off-gas product stream was analyzed by means of a modified Applied Automation Model 12 gas chromatograph (GC), whereas the liquid product was analyzed by means of a Hewlett-packard Model 5750 gas chromatograph with columns being packed with Porapak Q material. The various components of the liquid product separated by GC were confirmed by mass spectrometry.

EXAMPLE II

This example illustrates the conversion of methyl ethyl ketone and carbon monoxide to higher ketones, in the presence of a $CuO-ZnO-Al_2O_3$ catalyst.

In invention run 1, CO was charged with methyl ethyl ketone (MEK); in control run 2, $N_2$ was charged with methyl ethyl ketone at rates given in Example I. Results are summarized in Table I.

TABLE 1

|  | Run 1 (Invention) | Run 2 (Control) |
|---|---|---|
| % Conversion of MEK | 41 | 5.6 |
| Composition of Liquid Product: |  |  |
| Wt % of $C_4$ Hydrocarbons | 0.4 | — |
| Wt % of Methyl Ethyl Ketone | 63.1 | 94.3 |
| Wt % of $C_5$ Alcohols | 0.7 | 0.3 |
| Wt % of $C_5$ Ketones | 0.6 | — |
| Wt % of $C_6$ Alcohols | — | 1.0 |
| Wt % of $C_6$ Ketones | 3.5 | 0.5 |
| Wt % of $C_7$ Alcohols | — | 0.8 |
| Wt % of $C_7$ Ketones | 1.3 | 0.9 |
| Wt % of $C_8$ Alcohols | — | 1.2 |
| Wt % of $C_8$ Ketones | 26.8[1] | 1.2 |
| Wt % of Others | 3.6 | — |

[1]Mainly (about 95%) 5-methyl-heptanone-3.

Data in Table I demonstrate that the methyl ethyl ketone conversion was significantly higher when CO was present in the feed (Run 1) than when $N_2$ was present (Run 2). The % selectivity to $C_5$-$C_8$ ketones (wt % of $C_6$-$C_8$ ketones ÷ MEK conversion) was about 79% for invention run 1 and only about 46% for control run 2. The % selectivity to $C_8$ ketones was about 65% for invention run 1 and only about 21% for control run 2.

Reasonable variations and modifications are possible within the scope of the disclosure and the appended claims.

I claim:

1. A process for preparing higher ketones comprising the step of contacting a mixture comprising
    (a) at least one ketone selected from the group of ketones having from 3 to 5 carbon atoms per molecule, and
    (b) carbon monoxide with a catalyst composition comprising copper (II) oxide and zinc oxide, under such conditions as to form a reaction product comprising at least one higher ketone having at least one carbon atom per molecule more than the feed ketone in said mixture.

2. A process in accordance with claim 1, wherein said catalyst composition also comprises alumina.

3. A process in accordance with claim 1, wherein said at least one ketone having from 3 to 5 carbon atoms per molecule is methyl ethyl ketone.

4. A process in accordance with claim 3, wherein said reaction product comprises 5-methyl-heptanone-3.

5. A process in accordance with claim 1, wherein the weight ratio of CuO to ZnO in said catalyst composition ranges from about 1° to about 20:1 and the surface area of said catalyst composition ranges from about 20 m²/g to about 300 m²/g.

6. A process in accordance with claim 2, wherein the weight ratio of CuO to ZnO in said catalyst composition ranges from about 1:20 to about 20:1, the weight ratio of $Al_2O_3$ to (CuO plus ZnO) ranges from about 1:100 to about 10:1, and the surface area of said catalyst composition ranges from about 20 m²/g to about 300 m²/g.

7. A process in accordance with claim 1, wherein the weight ratio of CuO to ZnO in said catalyst composition ranges from 1:3 to about 3:1, and the surface area of said catalyst composition ranges from about 50 m²/g to about 200 m²/g.

8. A process in accordance with claim 2, wherein the weight ratio of CuO to ZnO in said catalyst composition ranges from about 1:3 to about 3:1, the weight ratio of $Al_2O_3$ to (ZnO plus CuO) ranges from 1:10 to about 2:1, and the surface area ranges from about 50 m²/g to about 200 m²/g.

9. A process in accordance with claim 1, wherein said catalyst composition has been pretreated by heating with a reducing gas under such conditions as to partially reduce copper (II) oxide before said contacting.

10. A process in accordance with claim 9, wherein said reducing gas is a free hydrogen containing gas, and said heating conditions comprise a temperature of about 350°–450° F. and a heating time of about 1–6 hours.

11. A process in accordance with claim 1, wherein the volume ratio of said at least one ketone having from 3 to 5 carbon atoms per molecule to carbon monoxide ranges from about 1:100 to about 20:1, measured at about 550° F. and about 15 psia.

12. A process in accordance with claim 5, wherein the volume ratio of said at least one ketone having from 3 to 5 carbon atoms per molecule to carbon monoxide ranges from about 1:20 to about 1:1, measured at about 550° F. and about 15 psia.

13. A process in accordance with claim 2, wherein the volume ratio of said at least one ketone having from 3 to 5 carbon atoms per molecule to carbon monoxide ranges from about 1:100 to about 20:1, measured at about 550° F. and about 15 psia.

14. A process in accordance with 6, wherein the volume ratio of said at least one ketone having from 3 to 5 carbon atoms per molecule to carbon monoxide ranges from about 1:20 to about 1:1, measured at about 550° F. and about 15 psia.

15. A process in accordance with claim 11, wherein said conditions comprise a reaction temperature ranging from about 200° C. to about 400° C., a reaction pressure ranging from about 1 to 5,000 psig, and a contact time of about 0.01 to about 60 minutes.

16. A process in accordance with claim 13, wherein said conditions comprise a reaction temperature ranging from about 200° C. to about 400° C., a reaction pressure ranging from about 1 to 5,000 psig, and a contact time of about 0.01 to about 60 minutes.

17. A process in accordance with claim 16, wherein said conditions further comprise a gas hourly space velocity of said mixture comprising at least one ketone having from 3–5 carbon atoms per molecule and CO ranging from about 100 to about 10,000 cc mixture/cc catalyst/hour.

18. A process in accordance with claim 12, wherein said at least one ketone having from 3–5 carbon atoms per molecule is methyl ethyl ketone and said reaction product comprises 5-methyl-heptanone-3.

19. A process in accordance with claim 1 comprising the additional step of separating at least a portion of said higher ketone from said reaction product.

20. A process in accordance with claim 19 comprising the additional step of recycling at least a portion of said reaction product, from which at least a portion of said higher ketone has been separated, to the reaction zone where the process in accordance with claim 1 occurs.

21. A process for preparing higher ketones comprising the step of contacting a mixture consisting essentially of
    (a) at least one ketone selected from the group of ketones having from 3 to 5 carbon atoms per molecule, and
    (b) carbon monoxide with a catalyst composition comprising copper (II) oxide and zinc oxide, under such conditions as to form a reaction product comprising at least one higher ketone having at least one carbon atom per molecule more than the feed ketone in said mixture.

* * * * *

UNITED STATES PATENT AND TRADEMARK OFFICE
CERTIFICATE OF CORRECTION

PATENT NO. :       4605775
DATED      :       August 12, 1986
INVENTOR(S) :      David J. Elliott It is certified that error appears in the above-identified patent and that said Letters Patent is hereby corrected as shown below:

Claim 5, column 5, line 32, delete "$1^O$" and insert therefor --- 1:20 ---.

Signed and Sealed this

Twenty-eighth Day of October, 1986

[SEAL]

Attest:

DONALD J. QUIGG

*Attesting Officer*     *Commissioner of Patents and Trademarks*